United States Patent [19]

Satoh et al.

[11] Patent Number: 4,617,292

[45] Date of Patent: Oct. 14, 1986

[54] PHARMACEUTICAL COMPOSITIONS AND METHOD FOR INHIBITING HISTAMINE RELEASE TOCOPHERYL GLYCOSIDE

[75] Inventors: Toshio Satoh; Hideki Miyataka, both of Tokushima; Yukimitsu Masamoto, Shiga; Takashi Asai, Takatsuki; Kenji Hasegawa, Ibaraki; Hisao Kakegawa, Tokushima, all of Japan

[73] Assignee: Sunstar Kabushiki Kaisha, Osaka, Japan

[21] Appl. No.: 755,777

[22] Filed: Jul. 17, 1985

[30] Foreign Application Priority Data

Jul. 21, 1984 [JP] Japan ................... 59-151895

[51] Int. Cl.$^4$ ................. A61K 31/70; C07H 15/26
[52] U.S. Cl. ................... 514/27; 536/4.1; 536/8; 536/8.8; 536/18.1
[58] Field of Search .............. 536/4.1, 18.1, 8, 8.8, 536/13; 514/27

[56] References Cited

U.S. PATENT DOCUMENTS 2,616,889  11/1952  Velluz et al. ................. 536/18.1
3,652,536   3/1972  Sebek et al. ................... 536/13

OTHER PUBLICATIONS

Yamamoto et al., Abstracts of the 103rd Annual Meeting of the Pharmaceutical Society of Japan, Apr. 4–6, 1983.

Primary Examiner—Johnnie R. Brown

[57] ABSTRACT

A pharmaceutical composition for producing antiallergic activity containing as an active ingredient a certain tocopherol derivative having a sugar residue at 6-position of the 3,4-dihydrobenzopyrane ring thereof. A method for producing antiallergic activity using such a tocopherol derivative and some novel tocopherol derivatives are also disclosed.

25 Claims, No Drawings

PHARMACEUTICAL COMPOSITIONS AND METHOD FOR INHIBITING HISTAMINE RELEASE TOCOPHERYL GLYCOSIDE

FIELD OF THE INVENTION

The present invention relates to a pharmaceutical composition and a method for producing antiallergic activity by using certain tocopheryl glycosides. In addition, the present invention also relates to certain novel tocopheryl glycosides.

BACKGROUND OF THE INVENTION

Various antiallergic agents have been hitherto known in treatment of allergic diseases but, as the mechanism of allergic reactions which cause allergic diseases has been made clear, it has been still requested to develop allergic agents which can directly inhibit allergic reactions, rather than symptomatic allergic agents.

During the study of pharmacological activities of tocopherol and its derivatives, the present inventors have surprisingly found that certain tocopheryl glycosides exhibit excellent activity to inhibit allergic reactions, particularly, to inhibit release of histamine from mast cells due to an antigen-antibody reaction and, therefore, they are useful as antiallergic agents.

OBJECTS AND SUMMARY OF THE INVENTION

One object of the present invention is to provide a pharmaceutical composition for producing antiallergic activity which contains as an active ingredient a certain tocopheryl glycoside.

Another object of the present invention is to provide a method for producing antiallergic activity.

Still another object of the present invention is to provide certain novel tocopheryl glycosides, some of which are useful as the active ingredient of the pharmaceutical composition of the present invention and the others are useful as intermediates for producing the tocopheryl glycosides to be used as the active ingredient.

These objects as well as other objects and advantages of the present invention will become apparent to those skilled in the art from the following description.

According to the present invention, there is provided a pharmaceutical composition for producing antiallergic activity which comprises an effective amount of a compound of the formula:

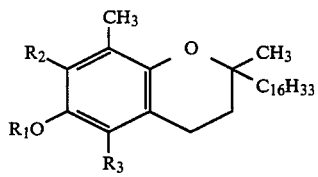
[I]

wherein $R_1$ is a residue of a sugar selected from the group consisting of glucose, galactose, cellobiose, mannose, maltose and lactose; and $R_2$ and $R_3$ are the same or different and each is hydrogen or methyl, and a pharmaceutically acceptable carrier or diluent. The method for producing antiallergic activity of the present invention comprises orally or parenterally administering or topically applying the compound of the formula [I], preferably, in the form of a pharmaceutical composition to an animal subject requiring such an activity including human being.

The compound of the formula [I] wherein $R_1$ is glucose residue, galactose residue or cellobiose residue is known but its antiallergic activity is not known in the prior art.

On the other hand, the compound of the formula [I] wherein $R_1$ is mannose residue, maltose residue or lactose residue is novel and, therefore, including an intermediate compound for the production thereof, the present invention is also provided the novel compound of the formula:

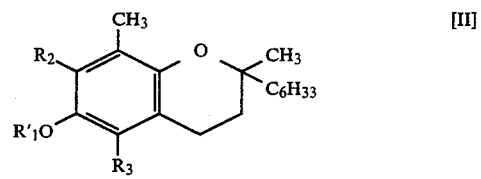
[II]

wherein $R'_1$ is a residue of a sugar selected from the group consisting of mannose, maltose, lactose and its acetylated derivative; and $R_2$ and $R_3$ are as defined with respect to the formula [I].

DETAILED DESCRIPTION OF THE INVENTION

In the compounds of the formulas [I] and [II], the group $-C_{16}H_{33}$ at 2-position of the 3,4-dihydrobenzopyran ring represents 4,8,12-trimethyltridecyl group of the side-chain at 2-position of tocopherol. Although tocopherol as well as the sugar residue introduced into the 6-hydroxy group can exist as isomers, all the isomers including a mixture thereof and an isolated isomer are included within the scope of the present invention.

Preferably, both $R_2$ and $R_3$ are methyl or hydrogen. That is, they are α- and δ-tocopheryl glycosides.

The representatives of the compound of the formula [I] are as follows:
  dl-α-tocopherylglucoside;
  dl-α-tocopherylgalactoside;
  dl-α-tocopherylcellobioside;
  dl-α-tocopherylmannoside;
  dl-α-tocopherylmaltoside;
  dl-α-tocopheryllactoside;
  d-δ-tocopherylglucoside;
  d-δ-tocopherylgalactoside;
  d-δ-tocopherylmannoside;
  d-δ-tocopherylmaltoside; and
  d-δ-tocopheryllactoside.

The compound of the formula [I] inhibits an allergic reaction, for example, histamine release reaction from mast cells due to an antigen-antibody reaction to exhibit excellent antiallergic activity.

The activity of the compound to inhibit the histamine release reaction can be determined in vitro by the folowing test.

Wister male rats (body weight: 150 to 180 g) were actively sensitized by subcutaneously administering ovalbumin (1 mg) and a diphtheria and tetanus toxoid combined with pertussis vaccine (0.5 ml, prepared by Kitasato Laboratories, Japan) containing $2 \times 10^{10}$ cells/ml of *Bordetella pertussis* in a pad of each rat. After 14 days from sensitization, animals were sacrificed by decapitation and bloodletting. A culture medium for mast cells containing 100 μg/ml of bovine serum albumin (NaCl 150 mM, KCl 3.7 mM, $Na_2HPO_4$ 4 mM, KH$_2$PO$_4$ 3.5 mM, CaCl$_2$ 1 mM, glucose 5.6 mM, bovine serum albumin 0.1%, heparin 10 units/ml; hereinafter referred to as MCM) was injected intraperitoneally in an amount of 10 ml/animal. After massaging for about 90 seconds, each animal was subjected to celiotomy to collect an intraperitoneal cell suspension. The suspension was centrifuged at 500 r.p.m. at 4° C. for 5 minutes and the resulting precipitate was washed twice with ice-cooled MCM. Then, MCM was added to the precipitate to prepare a cell suspension containing about $5 \times 10^4$ mast cells/ml. MCM (1.3 ml) was added to the cell suspension (0.3 ml) and, further, phosphatidyl serine was added in such an amount that the final concentration thereof is 30 μg/ml. Then, a solution of a compound to be tested in ethanol prepared at the time of performing the test (0.02 ml) was added and the mixture was pre-incubated at 37° C. for 5 minutes. As a control, the same operation was repeated provided that ethanol (0.02 ml) was used instead of the ethanol solution of the test compound. Then, a solution of antigenic ovalbumin in physiological saline solution (final reaction concentration of antigenic ovalbumin: $10^{-4}$ g/ml) was added and the resulting mixture was incubated at 37° C. for 10 minutes. The reaction was quenched with ice-cooling and the reaction mixture was centrifuged at 2,500 r.p.m. for 10 minutes to obtain a supernantant and a precipitate. According to the method described by M. Komatsu, Allergy, 27, 67 (1978), the amount of histamine in both the supernatant and the precipitate were determined by fluorometry.

The percentage of the histamine content in the supernatant based on the total histamine content in the cells is considered as the histamine release rate.

The activity of a test compound to inhibit release of histamine can be expressed as its histamine release inhibition rate (%) calculated according to the following equation. All results were corrected for the "spontaneous" (antigen independent) release mesured in a sample to which was added MCM in place of antigenic ovalbumin.

$$I = [1 - (R_t - R_s)/(R_c - R_s)] \times 100$$

wherein I is histamine release inhibition rate (%); $R_t$ is histamine release of a test compound; $R_c$ is histamine release of the control; and $R_s$ is spontaneous release.

In this test, the representative compound of the formula [I], dl-α-tocopherylglucoside, showed 50% inhibition of histamine release at a concentration of about 50 μg/ml, and dl-α-tocopherylmannoside showed 50% inhibition at a concentration of about 15 μg/ml.

By the way, the compounds of the formula [I] have very low toxicity and, for example, LD$_{50}$ values of both dl-α-tocopherylglucoside and dl-α-tocopherylmannoside are more than 5,000 mg/kg (p.o.) and more than 500 mg/kg (i.p.).

The pharmaceutical composition for producing antiallergic activity of the present invention can be prepared according to a conventional technique by incorporating an effective but non-toxic amount of the compound of the formula [I] with a conventional pharmaceutically acceptable carrier or diluent. Further, the pharmaceutical composition of the present invention can contain one or more other conventional additives such as binders, disintegrators, lubricants, agents for making the composition isotonic, emulsifiers, suspending agents, and stabilizers. The pharmaceutical composition of the present invention can be prepared in an appropriate form suitable for oral or parenteral administration or topical application. For example, it can be prepared in the form of tablets, powders, granules, syrups, injectable liquids, eye lotions, ointments, creams, emulsions, aqueous alcoholic solutions, aerosol, inhalants and the like. Preferably, it can be formulated in a dosage unit form containing 1 to 100 mg of the compound of the formula [I].

The method for producing antiallergic activity of the present invention is carried out by orally or parenterally administering or topically applying the compound of the formula [I], preferably, in the form of a pharmaceutical composition to an animal subject requiring such an activity including human being. It is preferable to administer 1 to 100 mg/kg of the compound of the formula [I] per a dose with a daily dosage regimen of 100 to 1,000 mg/kg of the compound of the formula [I].

As described above, the present invention also provides the novel compounds of the formula [II]. Among them, the compound wherein R'$_1$ is a residue of the acetylated sugar is useful as an intermediate for the production of the pharmaceutically active compound. Examples thereof are as follows:

6-O-(β-2,3,4,6-tetraacetylmannopyranosyl)-dl-α-tocopherol;

6-O-(4-O-α-d-2',3',4',6'-tetraacetylglucopyranosyl-2,3,6-triacetylglucopyranosyl)-dl-α-tocopherol;

6-O-(4-O-β-d-2',3',4',6'-tetraacetylgalactopyranosyl-2,3,6-triacetylglucopyranosyl)-dl-α-tocopherol;

6-O-(β-2,3,4,6-tetraacetylmannopyranosyl)-d-δ-tocopherol;

6-O-(4-O-α-d-2',3',4',6'-tetraacetylglucopyranosyl-2,3,6-triacetylglucopyranosyl)-d-δ-tocopherol; and 6-O-(4-O-δ-d-2',3',4',6'-tetraacetylgalactopyranosyl-2,3,6-triacetylgluocpyranosyl)-d-δ-tocopherol.

The compounds of the formulas [I] and [II] can be prepared according to Helferich method which is a known arylglycoside production method.

That is, tocopherol is reacted with a desired peracetylated sugar in a suitable solvent by heating at an elevated temperature, for example, 80° to 100° C. for 3 to 7 hours. By this reaction, the acetylated derivatives which are the intermediate compounds for the production of the compounds of the formula [I] including those of the formula [II] wherein R'$_1$ is acetylated sugar residue can be obtained. This reaction suitably proceeds when ethylene glycol diacetate or nitrobenzene is used as the solvent and p-toluene sulfonic acid is added as a catalyst.

Tocopherol used as the starting material may be α-, β-, γ- or δ-tocopherol. A peracetylated sugar is known or can be prepared by acetylating a desired sugar according to a known acetylation method.

The acetylated derivative thus obtained is deacetylated according to a standard method, for example, by heating under reflux in absolute methanol in the presence of sodium methoxide and then treating with an ion exchange resin such as Amberlite IR-120 (H+type) to give the compound of the formula [I]. These compounds can be obtained in the form of stable crystals which are soluble in organic solvents such as alcohols, chloroform, benzene and the like and slightly soluble in water and can be further purified according to a standard method such as recrystallization.

The following examples further illustrate the present invention in detail but are not to be construed to limit the scope thereof.

EXAMPLE 1

6-O-(β-2,3,4,6-Tetraacetylmannopyranosyl)-dl-α-tocopherol dl-α-Tocopherol (10 g, 23.25 mmole) and β-D-mannopyranose pentaacetate (3.3 g, 8.46 mmole) were dissolved in nitrobenzene (5 ml). p-Toluene sulfonic acid (75 mg, 0.44 mmole) was added to the solution and the atmosphere was replaced by nitrogen. The mixture was reacted in an oil bath at 90° C. under reduced pressure of 20 mmHg. Progress of the reaction was monitored by TLC [benzene-ethyl acetate (10:1)]. After 5 hours, benzene (100 ml) was added to the reaction mixture and the mixture was washed with water (3×100 ml) and saturated brine (3×100 ml). The mixture was dried with anhydrous sodium sulfate and the benzene layer was evaporated under reduced pressure to give a dark brown oil (13 g).

The oil (13 g) was chromatographed on a column of silica gel (550 g) and eluted with benzene-ethyl acetate (9:1) to give the title compound (2.4 g) as a yellow oil, yield: 38%.

TLC [benzene:ethyl acetate (10:1)]: $R_f=0.3$ (single spot).

Ir $\nu_{max}^{KBr}$: 1,756 (C=O) cm$^{-1}$.

MS: m/z 760 (M+).

EXAMPLE 2 dl-α-Tocopherylmannoside

The product of Example 1 (2.4 g, 3.12 mmole) was dissolved in dried methanol (8 ml) and 0.1N sodium methoxide (2 ml) was added to the solution. The solution was heated under reflux in a water bath. After 5 minutes, the reaction mixture was cooled and neturalized with Amberlite IR-120 (H+ type). After decolorization with charcoal, the reaction mixture was filtered and the filtrate was evaporated under reduced pressure to give the title compound (1.23 g) as white crystals, yield: 68%. The crystals thus obtained was recrystalized from acetone to give the further purified title compound (0.95 g), yield: 19%.

m.p.: 128°–130° C.

TLC [chloroform-methanol (5:1)]: $R_f=0.3$.

IR $\nu_{max}^{KBr}$: 3,390, 1,160 (OH; sugar) cm$^{-1}$.

MS: m/z 592 (M+).

EXAMPLE 3

6-O-(4-O-α-d-2',3',4',6'-Tetraacetylglucopyranosyl-2,3,6-triacetylglucopyranosyl)-dl-α-tocopherol dl-α-Tocopherol (10 g, 23.2 mmole) and β-D-maltopyranose octaacetate (6.6 g, 9.7 mmole) were dissolved in nitrobenzene (7 ml) and p-toluene sulfonic acid (150 mg, 0.87 mmole) was added to the solution. The atmosphere was replaced with nitrogen and the mixture was reacted in an oil bath at 90° C. under reduced pressure of 20 mmHg. After 5 hours, benzene (100 ml) was added to the reaction mixture and the mixture was washed with water (3×100 ml) and saturated brine (3×100 ml). The mixture was dried with anhydrous sodium sulfate and the benzene layer was evaporated under reduced pressure to give a drak brown oil (22 g).

The oil (22 g) was chromatographed on a column of silica gel (550 g) and eluted with benzene-ethyl acetate (9:1) to give the title compound (2.1 g) as a yellow oil, yield: 28%.

TLC [benzene-ethyl acetate (10:1)]: $R_f=0.3$ (single spot).

IR $\nu_{max}^{KBr}$: 1,770 (C=O) cm$^{-1}$.

EXAMPLE 4 dl-α-Tocopherylmaltoside

The product of Example 3 (2.1 g, 2.0 mmole) was dissolved in dried methanol (10 ml) and 0.1N soidum methoxide was added to the solution. The mixture was heated under reflux in a water bath. After 5 minutes, the reaction mixture was neutralized with Amberlite Ir-120 (H+ type). After decolorization with charcoal, the reaction mixture was filtered and the filtrate was evaporated under reduced pressure to give the title compound (1.2 g) as white crystals, yield: 80%. The crystals thus obtained were recrystallized from methanol to give the purified title compound (0.84 g), yield: 11%.

m.p.: 145°–147° C.

TLC [chloroform-methanol (5:1)]: $R_f=0.3$ (single spot).

IR $\nu_{max}^{KBr}$: 3,390, 1,160 (OH; sugar) cm$^{-1}$.

MS: m/z754 (M+).

EXAMPLE 5

6-O-(4-O-β-d-2',3',4',6'-Tetraacetylgalactopyranosyl-2,3,6-triacetylglucopyranosyl)-dl-α-tocopherol dl-α-Tocopherol (10 g, 23.2 mmole) and β-D-lactopyranose octaacetate (6.6 g, 9.7 mmole) were dissolved in nitrobenzene (7 ml) and p-toluene sulfonic acid (140 mg, 0.82 mmole) was added to the solution. The atmosphere was replaced with nitrogen and the mixture was reacted in an oil bath at 90° C. under reduced pressure of 20 mmHg. After 5 hours, benzene (100 ml) was added to the reaction mixture and the mixture was washed with water (3×100 ml) and saturated brine (3×100 ml). After the mixture was dried with anhydrous sodium sulfate, benzene layer was evaporated under reduced pressure to give a dark brown oil (25 g).

The oil (25 g) was chromatographed on a column of silica gel (550 g) and eluted with benzene-ethyl acetate (9:1) to give the title compound (1.1 g) as a yellow oil, yield: 10%.

TLC [benzene-ethyl acetate (10:1)]: $R_f=0.3$ (single spot).

IR $\nu_{max}^{KBr}$: 1,760 (C=O) cm$^{-1}$.

EXAMPLE 6 dl-α-Tocopheryllactoside

The product of Example 5 (1.1 g, 1.0 mmole) was dissolved in dried methanol (10 ml) and 0.1N sodium methoxide was added to the solution. The mixture was heated under reflux in a water bath. After 5 minutes, the reaction mixture was neutralized with Amberlite IR-120 (H+) and decolorized with charcoal. The reaction mixture was filtered and the filtrate was evaporated under reduced pressure to give the title compound (0.6 g) as white crystals, yield: 85%.

m.p.: 147°–150° C.

TLC [chloroform-methanol (5:1)]:$R_f=0.3$ (single spot).

IR $\nu_{max}^{KBr}$: 3,390, 1,160 (OH; sugar) cm$^{-1}$.

EXAMPLE 7

6-O-(β-2,3,4,6-Tetraacetylmannopyranosyl)-d-δ-tocopherol d-δ-Tocopherol (10 g, 25 mmole) and β-D-mannopyranose pentaacetate (3.3 g, 8.86 mmole) were dissolved in nitrobenzene (5 ml) and p-toluene sulfonic acid (80 mg, 0.5 mmole) was added. The atmosphere was replaced with nitrogen and the mixture was reacted in an oil bath at 80° C. under reduced pressure of 20 mmHg. After 4 hours, benzene (100 ml) was added to the reaction mixture and the mixture was washed with water (3×100 ml) and saturated brine (3×100 ml). The mixture was dried with anhydrous soidum sulfate and the benzene layer was evaporated under reduced pressure to give a black oil (20 g).

The oil (20 g) was chromatographed on a column of silica gel (550 g) and eluted with benzene-ethyl acetate to give the title compound (3.8 g) as a yellow oil, yield: 61%.

TLC [benzene-ethyl acetate (10:1)]: $R_f = 0.3$ (single spot).

IR $\nu_{max}^{KBr}$: 1,760 (C=O) cm$^{-1}$.

MS: m/z732 (M$^{30}$).

EXAMPLE 8 d-δ-Tocopherylmannoside

The product of Example 7 (3.8 g, 5.2 mmole) was dissolved in dried methanol (8 ml) and 0.1N soidum methoxide (2 ml) was added to the solution. The mixture was heated under reflux in a water bath. After 5 minutes, the reaction mixture was neutralized with Amberlite IR-120 (H$_+$) and decolorized with charcoal. The reaction mixture was filtered and the filtrate was evaporated under reduced pressure to give the title compound (2.1 g) as white crystals, yield: 72%. The crystals were recrystallized from acetone to give the purified title compound (1.36 g), yield: 30%.

m.p.: 187°–189° C.

TLC [chloroform-methanol (5:1)]: $R_f = 0.3$ (single spot).

IR $\nu_{max}^{KBr}$: 3,390, 1,160 (OH, sugar) cm$^{-1}$.

MS: m/z564 (M+).

EXAMPLE 9

6-O-(4-O-α-d-2',3',4',6'-Tetraacetylglucopyranosyl-2,3,6-triacetylglucopyranosyl)-d-δ-tocopherol d-δ-Tocopherol (10 g, 25.0 mmole) and β-D-maltopyranose octaacetate (3.3 g, 8.86 mmole) were dissolved in nitrobenzene (5 ml) and p-toluene sulfonic acid (80 mg, 0.5 mmole) was added. The atmosphere was replaced with nitrogen and the mixture was reacted in an oil bath at about 80° C. under reduced pressure of 20 mmHg. After 4 hours, benzene (100 ml) was added to the reaction mixture and the mixture was washed with water (3×100 ml) and saturated brine (3×100 ml). After the mixture was dried with anhydrous sodium sulfate, the benzene layer was evaporated under reduced pressure to give a black oil (17 g).

The oil (17 g) was chromatographed on a column of silica gel (550 g) and eluted with benzene-ethyl acetate (9:1) to give the title compound (3.8 g) as a yellow oil, yield: 45%.

TLC [benzene-ethyl acetate (10:1)]: $R_f = 0.3$ (single spot).

IR $\nu_{max}^{KBr}$: 1,766 (C=O) cm$^{-1}$.

EXAMPLE 10 d-δ-Tocopherylmaltoside

The product of Example 9 (4.2 g, 4.1 mmole) was dissolved in dried methanol (10 ml) and 0.1N sodium methoxide (5 ml) was added to the solution. The mixture was heated under reflux in a water bath. After 5 minutes, the reaction mixture was neutralized with Amberlite IR-120 (H+ type) and decolorized with charcoal. The reaction mixture was filtered and the filtrate was evaporated under reduced pressure to give the title compound (2.4 g) as white crystals, yield: 82%. The crystals were recrystallized from acetone to give the purified title compound (1.3 g), yield: 19%.

TLC [chloroform-methanol (5:1)]: $R_f = 0.3$ (single spot).

IR $\nu_{max}^{KBr}$: 3,390, 1,160 (OH; sugar) cm$^{-1}$.

MS: m/z726 (M+).

EXAMPLE 11

6-O-(4-O-β-d-2',3',4',6'-Tetraacetylgalactopyranosyl-2,3,6-triacetylglucopyranosyl)-d-δ-tocopherol d-β-Tocopherol (10 g, 24.8 mmole) and β-D-lactopyranose octaacetate (6.6 g, 9.7 mmole) were dissolved in nitrobenzene (7 ml) and p-toluene sulfonic acid (130 mg, 0.8 mmole) was added to the solution. The atmosphere was replaced with nitrogen, the mixture was reacted in an oil bath at about 80° C. under reduced pressure of 20 mmHg. After 4 hours, benzene (100 ml) was added to the reaction mixture and washed with water (3×100 ml) and saturated brine (3×100 ml). After the mixture was dried with anhydrous soidum sulfate, the benzene layer was evaporated under reduced pressure to give a black oil (25 g).

The oil (25 g) was chromatographed on a column of silica gel (550 g) and eluted with benzene-ethyl acetate (9:1) to give the title compound (4.0 g) as a yellow oil, yield: 50%.

TLC [benzene-ethyl acetate (10:1)]: $R_f = 0.3$ (single spot).

IR $\nu_{max}^{KBr}$: 1,760 (C=O) cm$^{-1}$.

EXAMPLE 12

The product of Example 11 (4.0 g, 3.9 mmole) was dissolved in dried methanol (10 ml) and 0.1N sodium methoxide (5 ml) was added. The mixture was heated under reflux in a water bath. After 5 minutes, the reaction mixture was neutralized with Amberlite IR-120 (H+ type) and decolorized with charcoal. The reaction mixture was filtered and the filtrate was evaporated under reduced pressure to give the title compound (2.3 g) as white crystals, yield: 82%. The crystals thus obtained were further recrystallized from acetone to give the purified title compound (1.28 g), yield: 18%.

m.p.: 57°–60° C.

TLC [chloroform-methanol (5:1)]: $R_f = 0.3$ (single spot).

IR $\nu_{max}^{KBr}$: 3,390, 1,160 (OH, sugar) cm$^{-1}$.

MS: m/z726 (M+).

EXAMPLE 13

According to the same procedures as described in the above Examples and by using desired tocopherols and peracetylated sugars, the following compounds of the formula [I] are obtained through the corresponding acetylated derivatives.

dl-α-Tocopherylglucoside (m.p. 140°–141° C.);

dl-α-Tocopherylgalactoside (m.p. 176°–177° C.);
dl-α-Tocopherylcellobioside (m.p. >300° C.);
d-δ-Tocopherylglycoside (m.p. 46°–49° C.); and
d-δ-Tocopherylgalactoside (m.p. 140°–141° C.).

EXAMPLE 14

| Ingredients | Parts by weight |
| --- | --- |
| dl-α-Tocopherylglucoside | 30 |
| Potassium phosphate | 490 |
| Crystaline cellulose | 350 |
| Sodium carboxy methylcellulose | 120 |
| Magnesium stearate | 10 |

These ingredients were thoroughly mixed and directly tabletted to give tables for oral administration.

EXAMPLE 15

| Ingredients | Parts by weight |
| --- | --- |
| dl-α-Tocopherylgalactoside | 380 |
| Lactose | 480 |
| Polyvinylpyrrolidone | 45 |
| Hydroxypropylcellulose | 95 |

According to a standard wet granulation technique, granules were prepared from these ingredients.

EXAMPLE 16

| Ingredients | Parts by weight |
| --- | --- |
| dl-α-Tocopherylmannoside | 5 |
| Distilled water for injection | 950 |

The ingredients were admixed to prepare a solution and the solution was sterilized by filtration to obtain an injectable preparation.

EXAMPLE 17

| Ingredients | Parts by weight |
| --- | --- |
| d-δ-Tocopherylglucoside | 20 |
| Beeswax | 100 |
| Paraffin wax | 60 |
| Lanolin | 30 |
| Isopropyl myristate | 60 |
| Squalane | 80 |
| Liquid paraffin | 250 |
| Polyoxyethylene sorbitan monostearate | 18 |
| Propylene glycol | 50 |
| Borax | 7 |
| Water | 325 |

According to a standard method, an ointment was prepared from these ingredients.

EXAMPLE 18

| Ingredients | Parts by weight |
| --- | --- |
| d-δ-Tocopheryllactoside | 50 |
| Stearic acid | 20 |
| Cetanol | 5 |
| Lanolin | 20 |
| Isopropyl myristate | 20 |
| Squalane | 30 |
| Liquid paraffin | 80 |
| Polyoxyethylene cetyl ether | 17 |
| Triethanolamine | 10 |
| Glycerin | 40 |
| Flavor and Preservative | q.p. |
| Water | up to 1,000 parts |

According to a standard method, an emulsion preparation was prepared from these ingredients.

What is claimed is:

1. A method for inhibiting histamine release which comprises orally or patenterally administering or topically applying an effective amount of a compound of the formula:

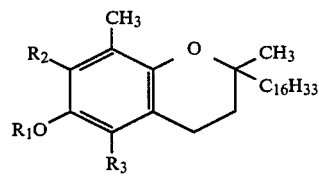

wherein $R_1$ is a residue of a sugar selected from the group consisting of glucose, galactose, cellobiose, mannose, maltose and lactose; $R_2$ and $R_3$ are the same or different and each is hydrogen or methyl, to an animal subject requiring said activity including human being.

2. A method according to claim 1, wherein the compound is dl-α-tocopherylglucoside.
3. A method according to claim 1, wherein the compound is dl-α-tocopherylgalalctoside.
4. A method according to claim 1, wherein the compound is dl-α-tocopherylcellobioside.
5. A method according to claim 1, wherein the compound is dl-α-tocopherylmannoside.
6. A method according to claim 1, wherein the compound is dl-α-tocopherylmaltoside.
7. A method according to claim 1, wherein the compound is dl-α-tocopheryllactoside.
8. A method according to claim 1, wherein the compound is d-δ-tocopherylglucoside.
9. A method according to claim 1, wherein the compound is d-δ-tocopherylgalactoside.
10. A method according to claim 1, wherein the compound is d-δ-tocopherylmannoside.
11. A method according to claim 1, wherein the compound is d-δ-tocopherylmaltoside.
12. A method according to claim 1, wherein the compound is d-δ-tocopheryllactoside.
13. A compound of the formula:

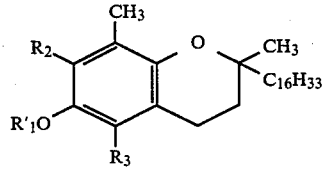

wherein $R_1$ is a residue of a sugar selected from the group consisting of mannose, maltose, lactose and an acetylated derivative thereof; $R_2$ and $R_3$ are the same or different and each is hydrogen or methyl.

14. The compound according to claim 13 which is dl-α-tocopherylmannoside.
15. The compound according to claim 13 which is dl-α-tocopherylmaltoside.

16. The compound according to claim 13 which is dl-α-tocopheryllactoside.

17. The compound according to claim 13 which is d-δ-tocopherylmannoside.

18. The compound according to claim 13 which is d-δ-tocopherylmaltoside.

19. The compound according to claim 13 which is d-δ-tocopheryllactoside.

20. The compound according to claim 13 which is 6-O-(β-2,3,4,6-tetraacetylmannopyranosyl)-dl-α-tocopherol.

21. The compound according to claim 13 which is 6-O-(4-O-α-d-2′,3′,4′,6′-tetraacetylglucopyranosyl-2,3,6-triacetylglucopyranosyl)-dl-α-tocopherol.

22. The compound according to claim 13 which is 6-O-(4-O-β-d-2′,3′,4′,6′-tetraacetylgalactopyranosyl-2,3,6-triacetylglucopyranosyl)-dl-α-tocopherol.

23. The compound according to claim 13 which is 6-O-(β-2,3,4,6-tetraacetylmannopyranosyl)-d-β-tocopherol.

24. The compound according to claim 13 which is 6-O-(4-O-α-d-2′,3′,4′,6′-tetraacetylglucopyranosyl-2,3,6-triacetylglucopyranosyl)-d-β-tocopherol.

25. The compound according to claim 13 which is 6-O-(4-O-β-d-2′,3′,4′,6′-tetraacetylgalactopyranosyl-2,3,6-triacetylglucopyranosyl)-d-β-tocopherol.

* * * * *